(12) United States Patent
Van Breda et al.

(10) Patent No.: US 11,052,521 B2
(45) Date of Patent: Jul. 6, 2021

(54) CRIMPING DEVICE

(71) Applicant: Strait Access Technologies Holdings (Pty) Ltd, Cape Town (ZA)

(72) Inventors: Braden Van Breda, Cape Town (ZA); Jean-Pierre Conradie, Durbanville (ZA); Mkhokheli Nkube, Bulawayo (ZW); Peter Zilla, Camps Bay (ZA); Deon Bezuidenhout, Cape Town (ZA); Bruce De Jongh, Sea Point (ZA)

(73) Assignee: Strait Access Technologies Holdings (PTY) LTD, Observatory (ZA)

( * ) Notice: Subject to any disclaimer, the term of this patent is extended or adjusted under 35 U.S.C. 154(b) by 166 days.

(21) Appl. No.: 16/337,468

(22) PCT Filed: Sep. 6, 2017

(86) PCT No.: PCT/ZA2017/050055
§ 371 (c)(1),
(2) Date: Mar. 28, 2019

(87) PCT Pub. No.: WO2018/064690
PCT Pub. Date: Apr. 5, 2018

(65) Prior Publication Data
US 2019/0232474 A1 Aug. 1, 2019

(30) Foreign Application Priority Data
Sep. 28, 2016 (ZA) .................. 2016/06732

(51) Int. Cl.
*B25B 27/10* (2006.01)
*A61F 2/95* (2013.01)
(Continued)

(52) U.S. Cl.
CPC ............... *B25B 27/10* (2013.01); *A61F 2/95* (2013.01); *A61F 2/9524* (2020.05);
(Continued)

(58) Field of Classification Search
CPC .... B25B 27/10; B21D 39/046; B21D 39/048; A61F 2240/001; A61F 2/9524
See application file for complete search history.

(56) References Cited

U.S. PATENT DOCUMENTS

| X758195 | | 4/1904 | Schweinert et al. |
|---|---|---|---|
| 2,409,549 | A * | 10/1946 | Djidics .................... F42D 1/04 86/40 |

(Continued)

FOREIGN PATENT DOCUMENTS

| EP | 1304095 | 4/2003 |
|---|---|---|
| EP | 2992857 | 3/2016 |
| SU | 437561 | 7/1974 |

OTHER PUBLICATIONS

Search Report and Written Opinion in International Application Serial No. PCT/ZA2017/050055 dated Nov. 27, 2017.

*Primary Examiner* — Edward T Tolan
(74) *Attorney, Agent, or Firm* — Haugen Law Firm PLLP

(57) ABSTRACT

A crimping device includes a housing defining a bore and at least three extendable mechanisms angularly equispaced about the axis of the bore. Each of the extendable mechanisms include: (i) a first elongate arm hingedly connected at or near a first axial end of the first arm to the housing; (ii) a second elongate arm hingedly connected at or near a first axial end of the second arm to the housing, wherein: the first axial ends of the first and second arms are displaceable relative to each other; and the first and second arms are hingedly connected at or near their second axial ends to each other. The crimping device further includes means for equi-displacing the first axial ends of coupled first and second arms relative to each other, thereby to configure the crimping device between: (i) a dilated condition in which the second axial ends of the first and second arms are maximally spaced from the bore axis; and (ii) a contracted condition in which the second axial ends of the first and second arms are minimally spaced from the bore axis.

13 Claims, 6 Drawing Sheets

(51) Int. Cl.
*B21D 39/04* (2006.01)
*A61F 2/82* (2013.01)

(52) U.S. Cl.
CPC .............. *B21D 39/048* (2013.01); *A61F 2/82* (2013.01); *A61F 2/9522* (2020.05); *A61F 2230/0023* (2013.01); *A61F 2240/001* (2013.01)

(56) References Cited

U.S. PATENT DOCUMENTS

| | | | |
|---|---|---|---|
| 2,887,222 A | 5/1959 | Latin et al. | |
| 2,986,192 A | 5/1961 | MacLeod | |
| 4,454,657 A | 6/1984 | Yasumi | |
| 4,498,218 A | 2/1985 | Friese | |
| 4,578,982 A | 4/1986 | Schroeck | |
| 5,261,263 A | 11/1993 | Whitesell | |
| 6,360,577 B2 | 3/2002 | Austin | |
| 6,925,847 B2 | 8/2005 | Motsenbocker | |
| 7,530,253 B2 | 5/2009 | Spenser et al. | |
| 7,748,248 B2 * | 7/2010 | Serrano | B21D 39/048 72/402 |
| 7,886,661 B1 | 2/2011 | Goff et al. | |
| 10,716,691 B2 * | 7/2020 | Saar | A61F 2/95 |
| 2005/0229670 A1 | 10/2005 | Perreault | |
| 2005/0234537 A1 | 10/2005 | Edin | |
| 2008/0053182 A1 | 3/2008 | Goff | |
| 2011/0056064 A1 * | 3/2011 | Malewicz | B25B 27/10 29/515 |
| 2012/0284986 A1 | 11/2012 | Kokish et al. | |
| 2013/0000548 A1 | 1/2013 | Eidenschink et al. | |
| 2013/0104366 A1 | 5/2013 | Skoel | |
| 2015/0336150 A1 | 11/2015 | Peterson et al. | |
| 2019/0091050 A1 * | 3/2019 | Walsh | A61F 2/95 |

* cited by examiner

CRIMPING DEVICE

BACKGROUND

The present invention relates to a crimping device. More particularly, the present invention relates to a device for crimping stents.

Various crimping devices are known. For example:
EP2,992,857 "Prosthetic valve crimping device", US2013/0104366 "Tissue prosthesis processing technology", US2015/0336150 "Crimping apparatus for crimping prosthetic valve with protruding anchors", U.S. Pat. No. 758,195 "Machine for contracting ferrules", U.S. Pat. No. 2,887,222 "Extrusion apparatus for sheathing electric cables", U.S. Pat. No. 2,986,192 "Apparatus and method for connecting couplings to hose" and U.S. Pat. No. 4,578,982 "Radial press for workpieces having a cylindrical exterior surface" describe crimping devices with a housing that defines a guide for channeling radial movement of bearing elements (i.e. elements that, in use, bear against the article to be crimped) along the guide.

A drawback of such crimping devices is that radial movement of bearing elements radially inwards of the radial inner periphery of the housing is largely limited by the radial length of the housing. In other words, radial extension of the bearing elements cannot exceed the length of the guide defined by the housing.

U.S. Pat. No. 6,925,847 "Hand held stent crimping apparatus and method", US2005/0234537 "Stent crimper", US2008/0053182 "Radial compression mechanism with optimum die-to-die gap", US2011/0056064 "Crimping device and method of use", US2013/0000548 "Devices and methods for abluminally coating medical devices", U.S. Pat. No. 5,261,263 "Crimping pliers with radially opposed jaws" and U.S. Pat. No. 7,530,253 "Prosthetic valve crimping device" describe crimping devices with a housing and bearing elements connected to the housing, wherein the bearing elements rotate relative to the housing, thereby causing the bearing elements to extend/retract radially.

A drawback of such crimping devices is that a small degree of radial rotation translates in a large degree of contraction, which high ratio generates significant mechanical stresses.

Furthermore, some of these crimping devices do not include overlapping bearing elements (that contact the article to be crimped). This absence of overlapping bearing elements exposes the article to be crimped to the risk of pinching while being crimped. Even further, where the crimping devices include bearing elements, as the crimping device is configured from the dilated condition to the contracted condition, the points of contact between the article to be crimped and the bearing elements spiral inwards, generating shear forces that could cause damage to the article to be crimped. Such shear forces and spiraling movement are particularly problematic where the article to be crimped is to be crimped on, or is connected to a stationary object (i.e. an object that is fixed in position against rotation, such as a balloon catheter).

US2012/0284986 "Stent crimping system and method", U.S. Pat. No. 4,454,657 "Aperture setting device" and U.S. Pat. No. 6,360,577 "Method for contracting, loading or crimping self-expanding and balloon expandable stent devices" describe devices that combine: (i) a housing that defines a guide for channeling radial movement of bearing elements along the guide; and (ii) a hinged connection between the housing and the bearing elements to permit rotation of the bearing elements relative to the housing.

Such crimping devices also suffer from the drawback that, as the crimping device is configured from the dilated condition to the contracted condition, the points of contact between the article to be crimped and the bearing elements on the crimping device spiral inwards, generating shear forces that could cause damage to the article to be crimped.

It should also be noted that the bearing elements of most known crimping devices are connected directly to the housing. An exception is the device described in U.S. Pat. No. 2,887,222 "Extrusion apparatus for sheathing electric cables", which device includes bearing elements pivotally connected to radially extending shanks. However, the bearing elements described in U.S. Pat. No. 2,887,222 do not overlap each other radially.

It is an object of the present invention to provide a crimping device that does not require a radially extending guide associated with the housing for regulating radial movement of bearing elements.

By providing a novel mechanism for moving bearing elements radially, the crimping device according to the present invention at least partially increases the radial displacement of the bearing element proportional to the radial length of the housing when compared to most prior art crimping devices (with the possible exception of the crimping device described in U.S. Pat. No. 2,887,222).

It is a further object of the present invention to provide a crimping device that has a non-linear rotation-to-contraction ratio. In other words, as an actuating handle configures the crimping device from a dilated condition to a contracted condition, the ratio of [handle rotation]:[contraction of the bore defined by the crimping device] reduces. Since the crimping force profile generally increases as the crimped device is contracted, this non-linear ratio "flattens-out" the force required to configure the crimping device from the dilated condition to the contracted condition.

It is an even further object of the invention to provide a crimping device wherein, as the crimping device is configured from the dilated condition to the contracted condition, the points of contact between the article to be crimped and the bearing elements on the crimping device move substantially radially inwards (instead of spiraling inwards), thereby reducing the shear forces to which the article to be crimped is subjected during crimping.

SUMMARY OF THE INVENTION

According to a preferred embodiment of the invention, there is provided a crimping device that includes:
- a housing defining a bore; and
- at least three extendable mechanisms angularly equispaced about the axis of the bore, each of which extendable mechanism including:
    - a first elongate arm hingedly connected at or near a first axial end of the first arm to the housing;
    - a second elongate arm hingedly connected at or near a first axial end of the second arm to the housing, wherein:
    - the first axial ends of the first and second arms are displaceable relative to each other; and
    - the first and second arms are hingedly connected at or near their second axial ends to each other; and
- means for equi-displacing the first axial ends of coupled first and second arms relative to each other, thereby to configure the crimping device between: (i) a dilated condition in which the second axial ends of the first and second arms are maximally spaced from the bore axis; and (ii) a contracted condition in which the second axial ends of the first and second arms are minimally spaced from the bore axis.

Typically, in respect of each extendable mechanism, the hinged connection of the first and second arms to each other is radially closer to the axis of the bore than the first axial ends of the first and second arms.

Generally, when the crimping device is in the contracted condition, in respect of each extendable mechanism, the second axial ends of the first and second arms protrude into the bore, with the hinged connection of the first and second arms spaced radially inwards of the inner radial periphery of the housing.

Typically, the first and second arms are of the same length.

Generally, each extendable mechanism further includes a bearing element extending from the first arm and/or the second arm at or near the second axial end of the first arm and/or the second arm.

Optionally, in respect of each extendable mechanism, the bearing element extends hingedly from the first arm and/or the second arm.

Preferably, in respect of each extendable mechanism, the bearing element is radially closer to the axis of the bore than the second axial ends of the first and second arms.

Typically, adjacent bearing elements overlap each other radially.

Optionally, adjacent bearing elements are slideably secured to each other. Alternatively, each extendable mechanism may further include biasing means for biasing at least one bearing element towards an adjacent radially outwards bearing element.

Preferably, the radial inner surface of each bearing element defines a curve along at least a portion of its length to enable contact between adjacent bearing elements as the crimping device is configured between the dilated and contracted conditions.

Optionally, in respect of each extendable mechanism, the first axial ends of the first and second arms are movable relative to each other along a virtual arc having a centre coincident with the axis of the bore. Alternatively, in respect of each extendable mechanism:
the radial spacing of:
(i) the hinged connection of the first axial end of the second elongate arm to the housing on the one hand; and
(ii) the axis of the bore on the other hand,
remains constant as the crimping device is configured between the dilated and contracted conditions; and
the radial spacing of:
(i) the hinged connection of the first axial end of the first elongate arm to the housing on the one hand; and
(ii) the axis of the bore on the other hand,
reduces as the crimping device is configured from the dilated condition towards the contracted conditions.

The crimping device may further include a resilient member that biases the first axial end of the first arm radially towards the axis of the bore as the crimping device is configured from the dilated condition towards the contracted conditions.

BRIEF DESCRIPTION OF THE DRAWINGS

The invention will now be described in more detail, by way of examples only, with reference to the accompanying drawings in which.

DESCRIPTION OF THE INVENTION

Figure 1:
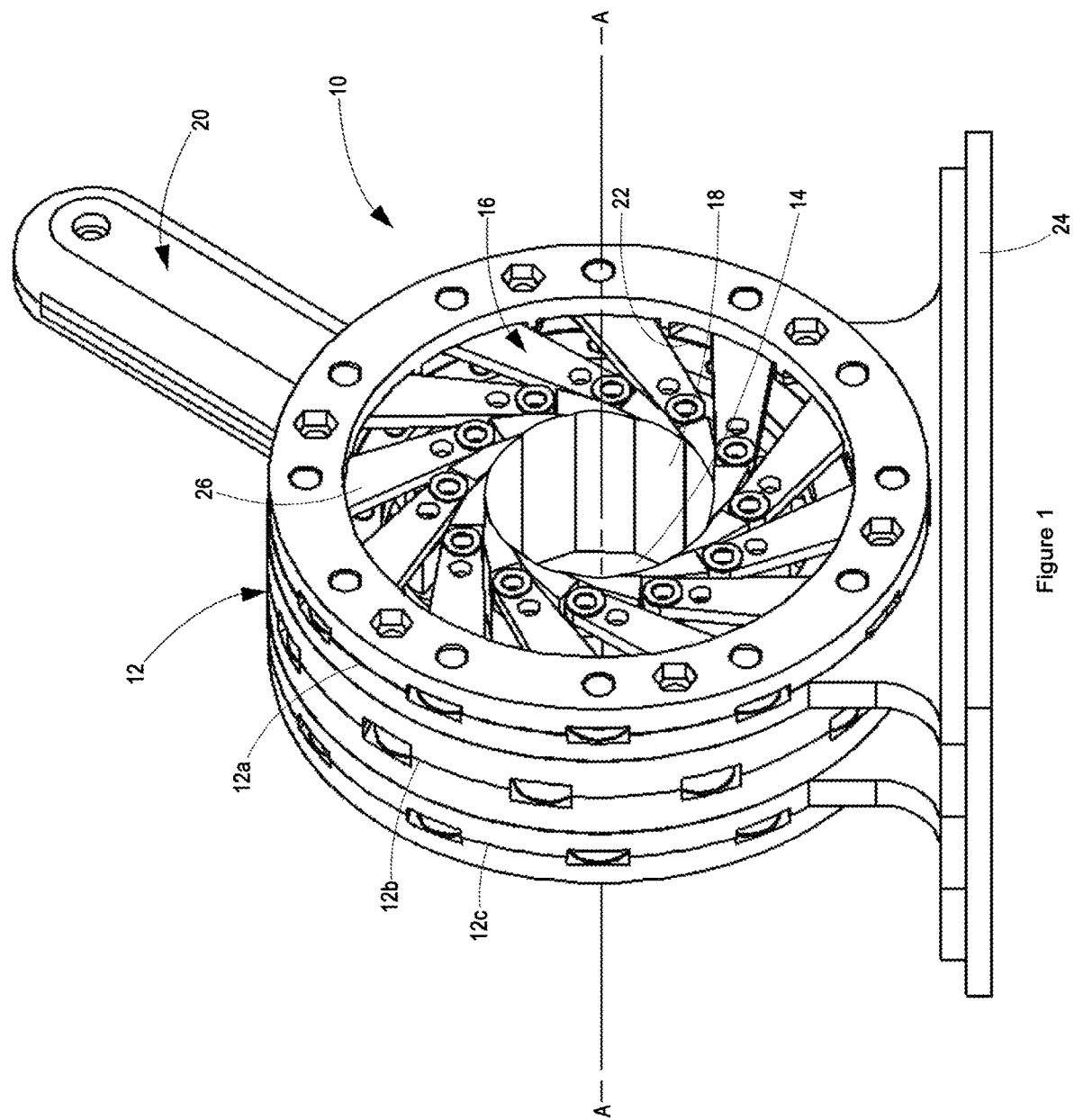
FIG. 1 is a perspective view of a crimping device according to a preferred embodiment of the invention, in a dilated condition.
Figure 2:
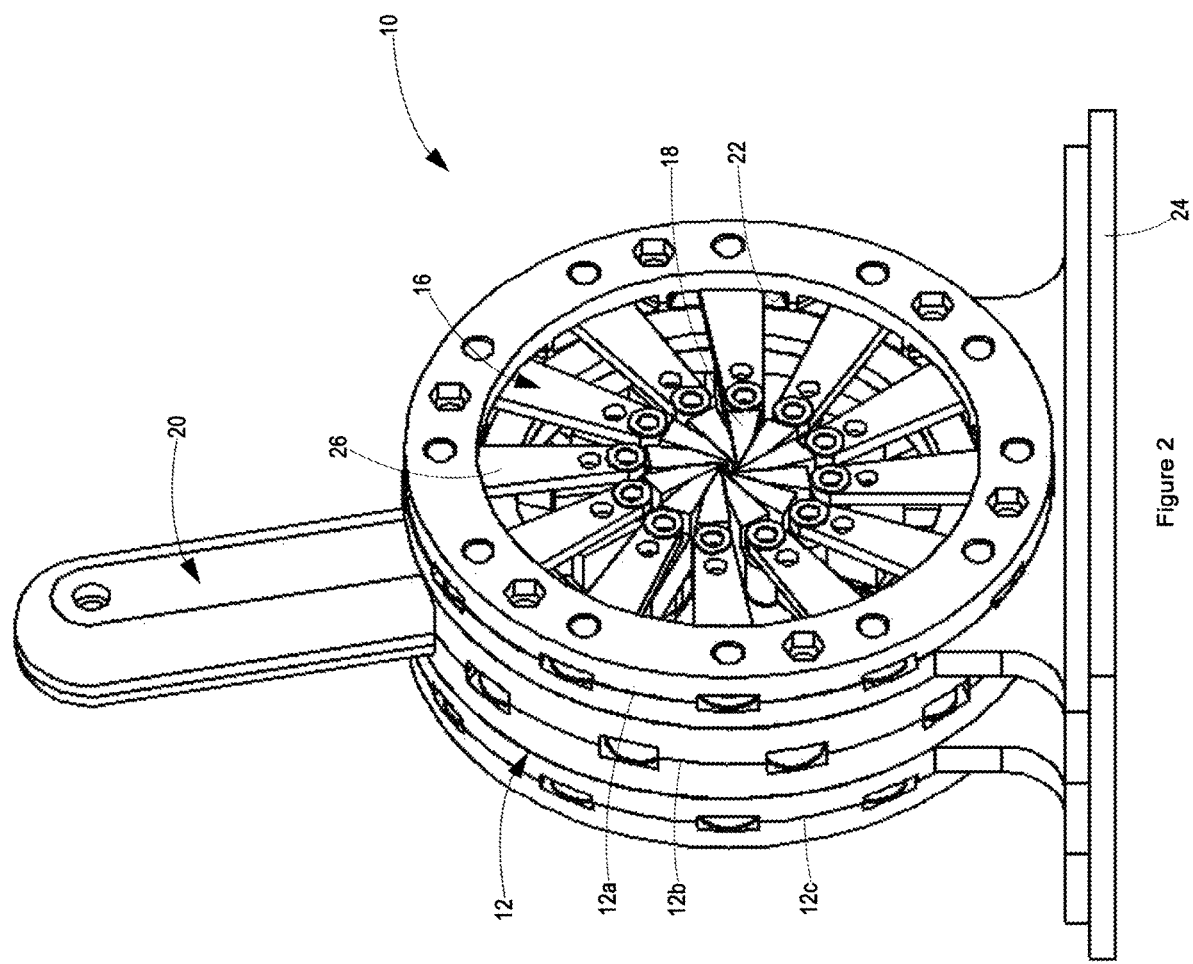
FIG. 2 is a perspective view of the crimping device in FIG. 1, in a contracted condition.
Figure 3:
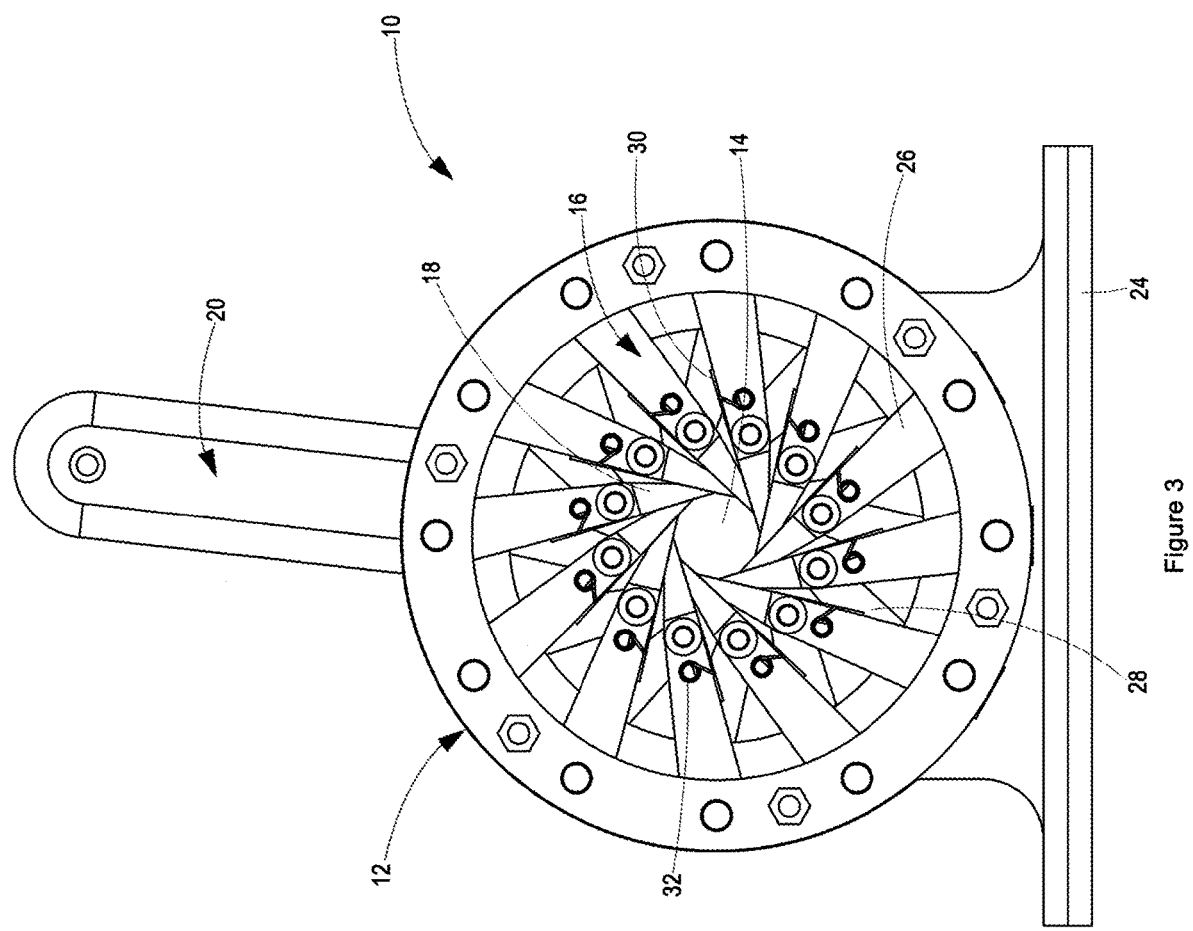
FIG. 3 is a front view of the crimping device in FIG. 1.
Figure 4:
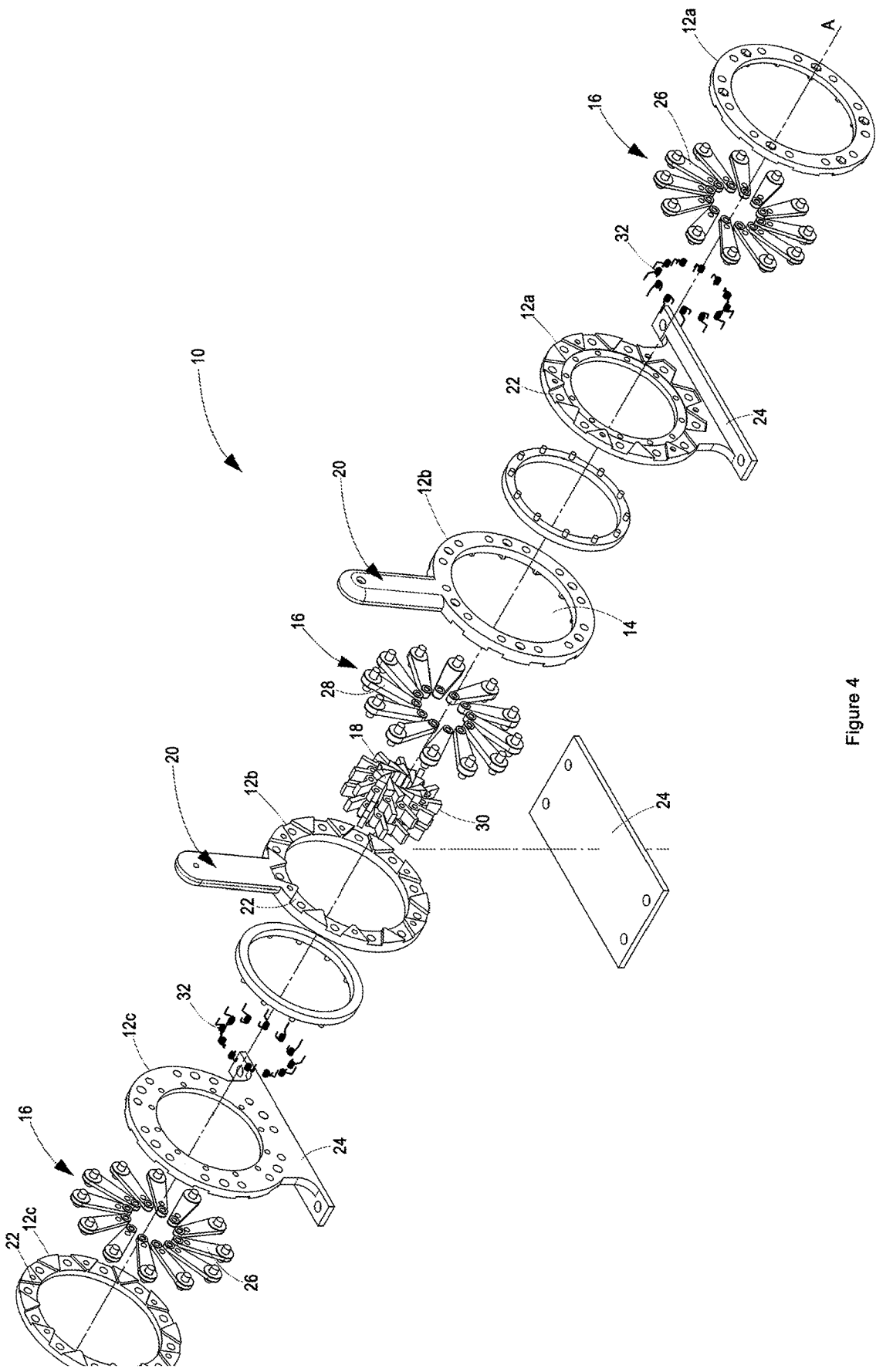
FIG. 4 is a perspective, exploded view of the crimping device in FIG. 1.

With reference to FIGS. 1 to 4 of the drawings, a preferred embodiment of a crimping device 10 for crimping articles, such as stents, includes a housing 12 that defines a bore 14, extendable elements 16 that move radially relative to the longitudinal axis A-A of the bore 14, bearing elements 18 and displacing means 20.

The housing 12 is generally cylindrical, defining a central circular bore 14 at its centre. The housing 12 is made of three substantially cylindrical parts 12*a*, 12*b* and 12*c*. The second part 12*b* is sandwiched between first and third parts 12*a* and 12*c* and rotatably secured thereto, such that the first and third parts 12*a* and 12*c* on the one hand are rotatable relative to the second part 12*b* on the other hand about the axis A-A of the bore 14. In other words, relative rotation (and not relative displacement) of the first and third parts 12*a* and 12*c* on the one hand and the second part 12*b* on the other hand is permitted. When the cylindrical parts 12*a*, *b* and *c* are secured to each other, they define annular grooves 22 on the inner radial peripheral surface of the housing 12, at: (i) the interface of the first part 12*a* and the second part 12*b*; and (ii) the interface of the second part 12*b* and the third part 12*c*. A base 24 that defines a planar surface, is provided at the operative bottom of the first and third portions 12*a* and 12*c*. In use, the base 24 is bolted to a support surface (e.g. the top of a table).

The extendable elements 16 are in the form of extendable mechanisms that are angularly equi-spaced about the axis of the bore 14. Each extendable mechanism comprises a first arm 26 and a second arm 28. Although the Figure show two sets of first arms 26 sandwiching the second arms 28, it will be appreciated that only one set of first arms 26 is required.

Both the first and second arms 26 and 28 are elongate, linear and of equal length. A first axial end of each of the first and second arms 26 and 28 is hingedly connected to the housing 12. More particularly: the first axial end of the first arm 26 is hingedly connected to the first part 12*a* of the housing 12, and extends along the annular groove 22 defined by the first part 12*a* of the housing 12; and the first axial end of the second arm 28 is hingedly connected to the second part 12*b* of the housing 12, and extends along the annular groove 22 defined by the second part 12*b* of the housing 12. Accordingly, relative rotation of the first and second parts 12*a* and 12*b* of the housing 12 causes the first axial ends of the first and second arms 26 and 28 to move relative to each other along a virtual arc having a centre coincident with the axis of the bore 14.

It will be appreciated that the Figures show an optional second set of second arms 28 having a first axial end hingedly connected to the third part 12*c* of the housing 12, however we do not focus on this optional second set of second arms 28 in this specification.

Each of the first and second arms 26 and 28 are arranged such that they extend from their first axial end towards the bore 14. The second axial ends of the first and second arms 26 and 28 are hingedly connected to each other. In respect of each extendable mechanism 16, the hinged connection of the first and second arms 26 and 28 to each other is radially closer to the axis of the bore 14 than the first axial ends of the first and second arms 26 and 28.

It will be appreciated that although the second axial ends of the first and second arms 26 and 28 have been shown as being directly hingedly connected to each other, the second axial ends of the first and second arms 26 and 28 may indirectly be hingedly connected to each other (e.g. via an intervening bridge) (not shown). Alternatively, a live hinge may connect the second axial ends of the first and second arms 26 and 28 to each other.

It will be appreciated that since: (i) the first axial end of each first arm 26 is hingedly connected to the first part 12a of the housing 12, and (ii) the first axial end of each second arm 28 is hingedly connected to the second part 12b of the housing 12, relative rotation of the first and second parts 12a and 12b of the housing 12 via the displacing means 20 causes equi-displacement of the first axial ends of all three coupled first and second arms 26 and 28 (i.e. first and second arms 26 and 28 that are joined to each other at their second axial ends to form a pair) relative to each other. Movement of the first axial ends of each coupled first and second arms 26 and 28 towards each other causes the hinged connection of these arms to each other (at their second axial ends) to spiral towards the axis A-A of the bore 14.

A bearing element 18 extends from at least one of the coupled first and second arms 26 and 28 at or near the second axial ends of such first and second arms 26 and 28. Preferably, each bearing element 18 is hingedly connected to the first and second arms 26 and 28 at the same position that the first and second arms 26 and 28 are connected to each other.

Each bearing element 18 is substantially wedge-shaped, connected to the first and second arms 26 and 28 at or near its thick end. The bearing elements 18 are radially closer to the axis of the bore 14 than the second axial ends of the first and second arms 26 and 28. A lever arm 30 extends from the thick end of the wedge shaped bearing element 18.

Adjacent bearing elements 18 overlap each other radially. The Figures show biasing means 32 in the form of springs, which induce biasing forces upon the lever arm 30 of the bearing elements to bias each bearing element 18 towards its radially outward adjacent bearing element 18. Alternatively (but not shown), each bearing element 18 could be slideably secured to adjacent bearing elements 18.

Figure 7:
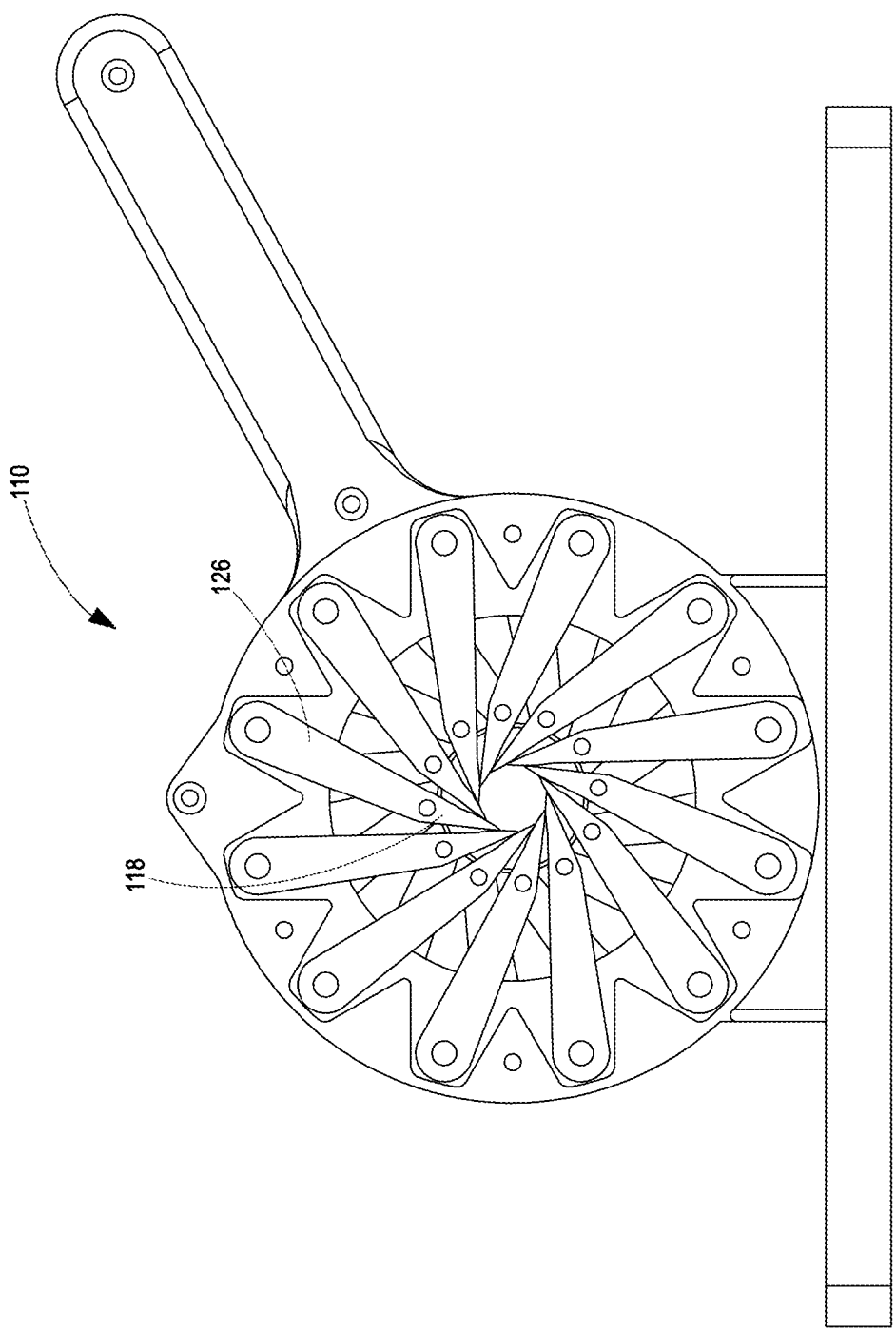
FIG. 7 is a side view of a crimping device according to an alternative embodiment of the invention.

Although the bearing elements 18 have been shown as being connected to each coupled first and second arm 26 and 28, it will be appreciated that: the bearing elements could be integrally formed with one of the arms 26 or 28 (i.e. extending from one of the arms 26 or 28). Further optionally, a living hinge could be formed between the arm 26 or 28 and the bearing element 18 that extends therefrom. An arrangement with the bearing element 118 extending from the first arm 126 is shown in FIG. 7. Preferably, the bearing element 118 and first arm 126 are made of a resilient material and formed such that, during assembly of the crimping device 110, the bearing element 118 is slightly deformed (i.e. angularly displaced relative to the first arm 126), which deformation induces the bearing element 118 to be biased towards its radially outward adjacent bearing element 118.

Optionally, the radially outward face of each bearing element 18 is not linear, instead the radially outward face of each bearing element 18 could comprise two coterminous linear portions defining an obtuse angle therebetween. Furthermore, the apex of each bearing element 18 (i.e. the end of each bearing element 18 distal the first or second arm 26 or 28 from which the bearing element 18 extends) preferably defines an angle calculated as follows: 360 degrees divided by the total number of bearing elements 18 forming part of the crimping device 10. The Figures also shows the radially inward face of each bearing element 18 and 118 defining a curve along at least a portion of the length of the bearing element 18 and 118.

Returning to FIGS. 1-4, the displacing means 20 comprises a handle that extends radially from the outer radial peripheral surface of the second part 12b of the housing 12. With the first and third parts 12a and 12c of the housing 12 secured in position to a support surface via the base 24, movement of the handle 20 about the axis of the bore 14 causes rotation of the second part 12b of the housing relative to both the first and third parts 12a and 12c of the housing 12.

In use:
The handle 20 on the crimping device 10 is rotated in a first direction about the axis of the bore 14 to configure the crimping device 10 to a dilated condition, in which the first axial ends of each coupled first and second arms 26 and 28 are maximally spaced from each other, with the second axial ends of each coupled first and second arms 26 and 28 (and the bearing elements 18) maximally spaced from the axis of the bore 14.

It should be noted that, when the crimping device 10 is in the dilated condition, the second axial end of each first and second arm 26 and 28 protrudes from the housing 12, into the bore 14. Accordingly, the bearing elements 18 (which are connected to the second axial ends of the first and second arms 26 and 28) are spaced radially inwards from the inner radial surface of the housing 12 with adjacent bearing elements radially overlapping each other.

A cylindrical article to be crimped, such as a stent, is axially inserted along the axis of the bore 14.

The handle 20 is rotated in a second direction about the axis of the bore 14 to cause the first axial ends of each coupled first and second arms 26 and 28 to move towards each other, and thereby cause the second axial ends of each coupled first and second arms 26 and 28 to move towards the axis of the bore 14 until the bearing elements 18 bear equally about the outer radial surface of the stent.

The handle 20 is further rotated in the second direction about the axis of the bore 14 to configure the crimping device 10 towards a contracted condition, in which the first axial ends of each coupled first and second arms 26 and 28 are minimally spaced from each other, with the second axial ends of each coupled first and second arms 26 and 28 (and the bearing elements 18) minimally spaced from the axis of the bore 14. As the crimping device 10 is configured towards the contracted condition, the stent is crimped (i.e. its diameter is reduced). Furthermore, the radial inner surface of each bearing element 18 defines a curve along at least a portion of its length to enable contact between adjacent bearing elements 18 as the crimping device 10 is configured between the dilated and contracted conditions. As the crimping device 10 is configured from the dilated condition to the contracted condition, adjacent bearing elements 18 are caused to slide over each other so as to ensure that the radial inner surface of the curved radial inner surface of the bearing elements 18 continue to present a substantially circular composite surface for bearing against the outer radial surface of the stent.

Focusing back on the first and second arms 26 and 28, the: (i) first axial end of the first arm 26; (ii) first axial end of the second arm 28; and (iii) hinged connection of the first arm 26 to the second arm 28 at or near the second axial ends of the first and second arms 26 and 28, form the corners of a triangle, which triangle defines: (a) a base that extends between the first axial ends of the first and second arms 26 and 28, and (b) a height measured from the midpoint of the base to the hinged connection of the first arm 26 to the second arm 28. It will be appreciated that shortening of the base causes an increase in the height. However, this relationship is not linear. In other words, as the base shortens, the following ratio decreases:

[Rate at which the height increases]/[Rate at which the base shortens]

Figure 5:
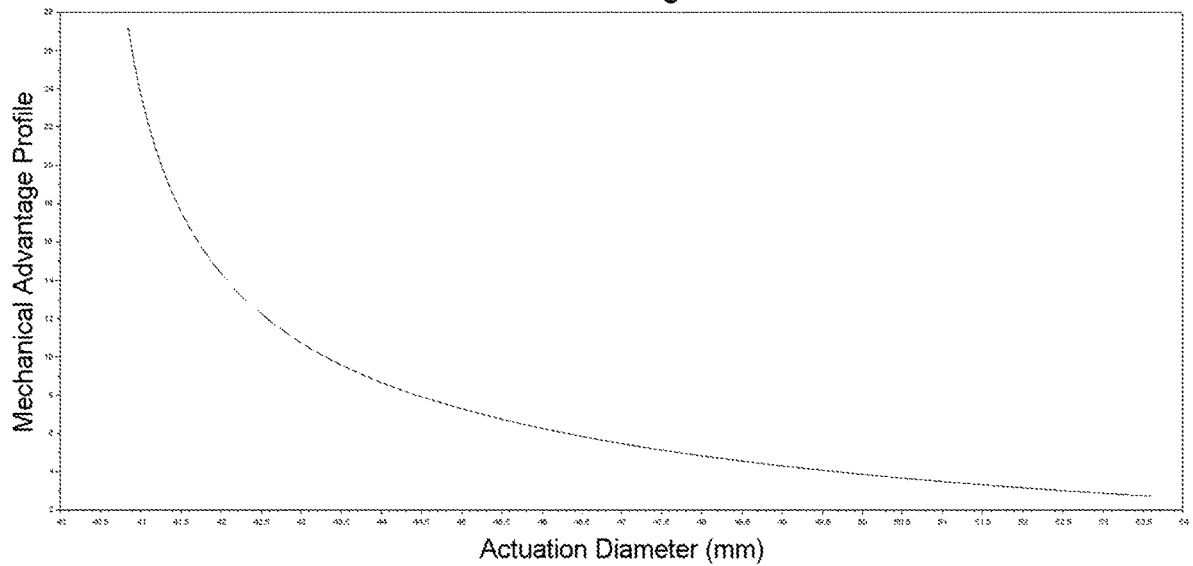
FIG. 5 is a graph showing the Mechanical Advantage v Actuation Diameter of the crimping device in FIG. 1.
Figure 6:
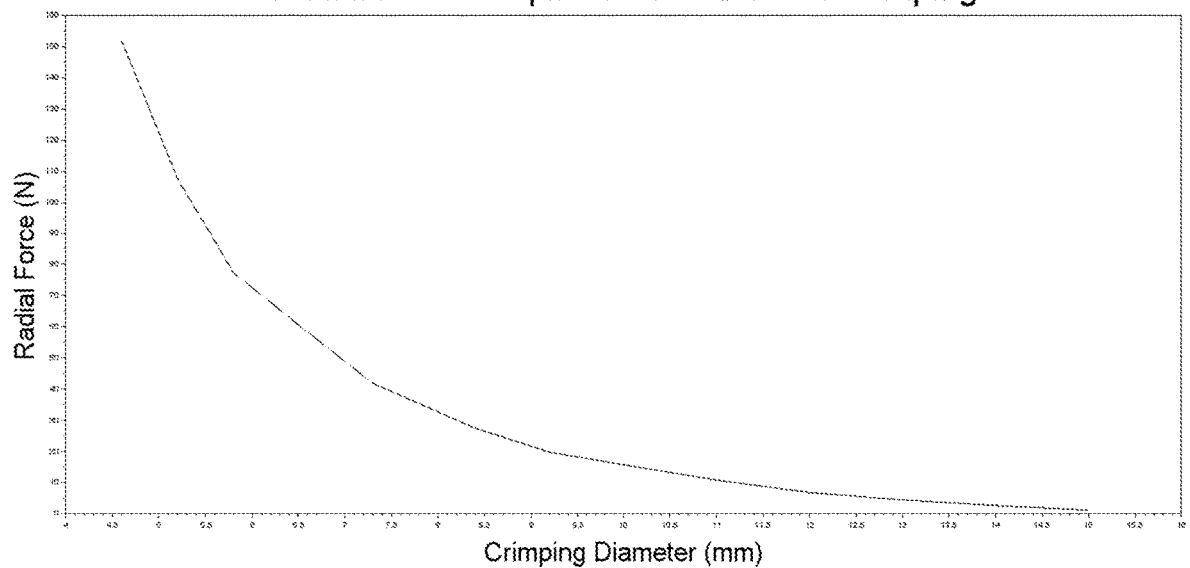
FIG. 6 is a graph showing Radial Force v Crimping Diameter of a typical stent to be crimped by the crimping device in FIG. 1.

Since articles to be crimped generally offer an increasing resistance to crimping during the crimping process, the non-linear relationship between: (i) movement of the first axial ends of the first and second arms 26 and 28 towards each other; and (ii) extension of the hinged connection of the first arm 26 to the second arm 28, "flattens-out" the force required to configure the crimping device 10 from the dilated condition to the contracted condition. This is best illustrated by the graphs in FIGS. 5 and 6. FIG. 5 shows the mechanical advantage of the crimping device 10—the mechanical advantage increases as the crimping device 10 is configured to a contracted condition; whereas FIG. 6 shows the radial force required to crimp a stent—the force required similarly increases as the stent undergoes crimping. It will be appreciated that the profile of the curves in FIGS. 5 and 6 are similar. As such, the force that a user applies to the handle 20 remains relatively constant during the crimping process.

It will be appreciated that, as the crimping device 10 is configured from the dilated condition to the contracted condition, displacement of the first end of only the second arm 28 towards the stationary (but hingedly rotating) first axial end of the first arm 26 causes the hinged connection of the first and second arms to spiral inwards along a spiral path. While, at the same time, contraction of the crimping device 10 causes the bearing elements 18 to rotate about their hinged connection to the first and second arms 26 and 28. Rotation of the bearing elements 18 relative to the first and second arms 26 and 28 substantially counteracts the spiral movement of the point of connection between the first and second arms 26 and 28, thereby ensuring that the points of contact between the article to be crimped and the bearing elements 18 move substantially radially inwards (instead of spiraling inwards). Such radial movement enables the article to be crimped about a stationary object (e.g. a balloon catheter).

Movement of the point of connection between the first and second arms 26 and 28 is best represented by the formula below:

$$OB = \sqrt{(R^2 - AT^2)} - \sqrt{(L^2 - AT^2)}$$

$$AT = \tfrac{1}{2} AC$$

Where:
OB is the distance from the point of connection between the first and second arms 26 and 28 to the longitudinal axis A-A of the bore 14;
R is the radius of the circumferential ring on which the first axial end of the first and second arms 26 and 28 are attached;
L is the length of the first and second arms 26 and 28; and
AC is the length of the base that extends between the first axial ends of the first and second arms 26 and 28.

It is also worth noting that overlapping of the bearing elements 18 reduces the risk of pinching of the article to be crimped, as the crimping device 10 is configured from the dilated condition to the contracted condition.

It should further be noted that, when the crimping device 10 is in the contracted condition, in respect of each extendable mechanism 16, the second axial ends of the first and second arms 26 and 28 protrude into the bore 14, with the hinged connection of the first and second arms 26 and 28 spaced radially inwards of the inner radial periphery of the housing 12.

Optionally, in respect of each extendable mechanism, the hinge between the first arm 26 and the housing 12 may include a pin that pivotally connected the first arm 26 and the housing 12. This pin may be covered by a resilient member, such as a flexible sleeve (not shown), which flexible sleeve is disposed between the radially inner pin and the radially outer housing 12. The flexible sleeve is deformable to permit the radial spacing of: (i) the hinged connection of the first axial end of the first arm 26 to the housing 12 on the one hand; and (ii) the axis A-A of the bore 14 on the other hand, to reduce as the crimping device 10 is configured from the dilated condition towards the contracted conditions (i.e. at least during such initial change in configuration). Since the hinged connection between the first axial end of the second arm 28 and the housing 12 does not include such a sleeve, the radial spacing of: (i) the hinged connection of the first axial end of the second arm 28 to the housing 12 on the one hand; and (ii) the axis A-A of the bore 14 on the other hand, remains constant as the crimping device 10 is configured between the dilated and contracted conditions. The addition of the flexible sleeve facilitates overlapping contact between adjacent bearing elements 18 during configuration of the crimping device 10 between the dilated and contracted conditions.

A prototype of the crimping device 10 was analysed and yielded the following ratio:

$$X/Y = 0.15$$

Where:
X is the radial thickness of the housing 12; and
Y is the radial protrusion of each bearing element 18 between the dilated and contracted conditions.

This 0.15 ratio is far superior to (i.e. much lower than) any prior art crimping device.

The crimping device 10 according to the present invention also presents advantages over the prior art devices in that, whereas prior art devices generally force bearing elements along a guide (with consequential wear on the bearing elements and guide), the crimping device 10 of the present invention concentrates wear at: (i) the hinged connections of the first axial ends of the first and second arms 26 and 28 to the housing 12; and (ii) the hinged connection of the first arm 26 to the second arm 28 at their second axial ends. Such wear and tear at the hinges is less aggressive than wear and tear along the guide.

The invention claimed is:

1. A crimping device including:
a housing defining a bore having an axis, which housing comprises a first part and a second part that are rotatable relative to each other about the axis; and
at least three extendable mechanisms angularly equispaced about the axis of the bore, each of which extendable mechanism including:
a first elongate arm hingedly connected at or near a first axial end of the first arm to the first part of the housing;
a second elongate arm hingedly connected at or near a first axial end of the second arm to the second part of the housing,
wherein:
the first axial ends of the first and second arms are circumaxially displaceable relative to each other;
the first and second arms are hingedly connected at or near their second axial ends to each other; and
the first and second arms are of the same length; and
means for rotating the first part of the housing relative to the second part of the housing about the axis and thereby circumaxially equi-displacing the first axial ends of coupled first and second arms relative to each other, thereby to configure the crimping device between: (i) a dilated condition in which the second axial ends of the first and second arms are maximally spaced from the bore axis; and (ii) a contracted condition in which the second axial ends of the first and second arms are minimally spaced from the bore axis.

2. A crimping device according to claim 1, wherein the hinged connection of the first and second arms to each other is radially closer to the axis of the bore than the first axial ends of the first and second arms.

3. A crimping device according to claim 2, wherein when the crimping device is in the contracted condition, the second axial ends of the first and second arms protrude into the bore, with the hinged connection of the first and second arms spaced radially inwards of an inner radial periphery of the housing.

4. A crimping device according to claim 3, wherein each extendable mechanism further includes a bearing element extending from at least one of the first arm and the second arm at or near the second axial end of the respective at least one of the first arm and the second arm.

5. A crimping device according to claim 4, wherein the bearing element extends hingedly from at least one of the first arm and the second arm.

6. A crimping device according to claim 5, wherein the bearing element is radially closer to the axis of the bore than the second axial ends of the first and second arms.

7. A crimping device according to claim 6, wherein adjacent bearing elements overlap each other radially.

8. A crimping device according to claim 7, wherein adjacent bearing elements are slideably secured to each other.

9. A crimping device according to claim 7, wherein each extendable mechanism further including biasing means for biasing at least one bearing element towards a radially outwardly adjacent bearing element.

10. A crimping device according to claim 7, wherein a radial inner surface of each bearing element defines a curve along at least a portion of its length to enable contact between adjacent bearing elements as the crimping device is configured between the dilated and contracted conditions.

11. A crimping device according to claim 10, wherein the first axial ends of the first and second arms are movable relative to each other along a virtual arc having a center coincident with the axis of the bore.

12. A crimping device according to claim 10, wherein:
the radial spacing of:
(i) the hinged connection of the first axial end of the second elongate arm to the second part of the housing; and
(ii) the axis of the bore,
remains constant as the crimping device is adjusted between the dilated and contracted conditions; and
the radial spacing of:
(i) the hinged connection of the first axial end of the first elongate arm to the first part of the housing on the one hand; and
(ii) the axis of the bore on the other hand,
reduces as the crimping device is configured from the dilated condition towards the contracted conditions.

13. A crimping device according to claim 12 further including a resilient member that biases the first axial end of the first arm radially towards the axis of the bore as the crimping device is configured from the dilated condition towards the contracted conditions.

* * * * *